United States Patent [19]
Porter et al.

[11] Patent Number: 5,709,838
[45] Date of Patent: Jan. 20, 1998

[54] SINGLE USE SAMPLING DEVICE

[75] Inventors: V. Christine Porter, Chatham; George H. Geisinger, Mountainside, both of N.J.

[73] Assignee: NIK Public Safety, Inc., Yulee, Fla.

[21] Appl. No.: 705,695

[22] Filed: Aug. 27, 1996

Related U.S. Application Data

[63] Continuation of Ser. No. 543,638, Oct. 16, 1995, abandoned, which is a continuation of Ser. No. 129,556, Sep. 29, 1993, abandoned, which is a continuation of Ser. No. 891,246, Jun. 1, 1992, abandoned.

[51] Int. Cl.⁶ ............................................. G01N 35/10
[52] U.S. Cl. ........................ 422/61; 422/99; 422/101; 436/808; 436/810
[58] Field of Search ........................... 422/58, 61, 99, 422/101; 436/808, 810, 901

[56] References Cited

U.S. PATENT DOCUMENTS

| | | | |
|---|---|---|---|
| 3,955,926 | 5/1976 | Fischer | 422/61 |
| 4,126,417 | 11/1978 | Edwards | 422/61 |
| 4,367,750 | 1/1983 | Levine | 422/61 |
| 4,900,663 | 2/1990 | Wie et al. | 435/7 |
| 4,981,653 | 1/1991 | Marino | 436/810 |
| 4,987,085 | 1/1991 | Allen et al. | 422/61 |
| 5,017,342 | 5/1991 | Haberzettl et al. | 436/810 |
| 5,082,626 | 1/1992 | Grage, Jr. | 422/56 |

*Primary Examiner*—Lyle A. Alexander
*Attorney, Agent, or Firm*—Abelman, Frayne & Schwab

[57] ABSTRACT

A single use sampling and sample delivery device for a test kit includes a strip having a first part and a second part. The first part has a first side and a second side, each side having a surface to serve as a spatula for collecting and placing a sample into a test kit. The second part serves as a handle for manipulating the first part. The first part which contains the sample may be readily separated from the second part, then left in the container. Alternate embodiments of the device include addition of an adhesive coating or a foam and adhesive coating to the first part, both employing a release covering to protect the sample surface from contamination prior to use. The device may be individually packaged or supplied in a pack containing a plurality of strips.

13 Claims, 5 Drawing Sheets

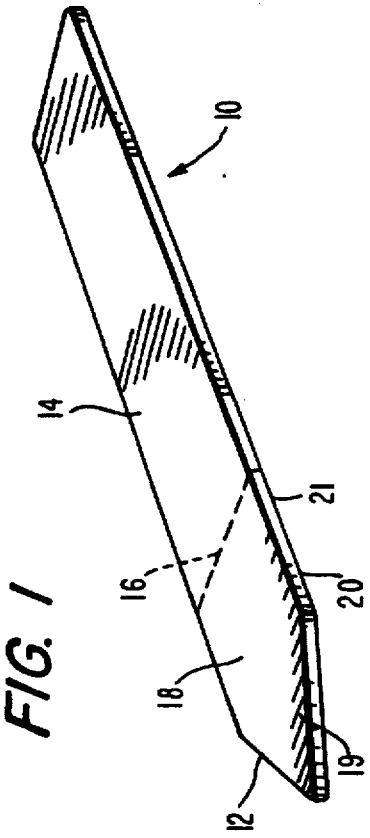
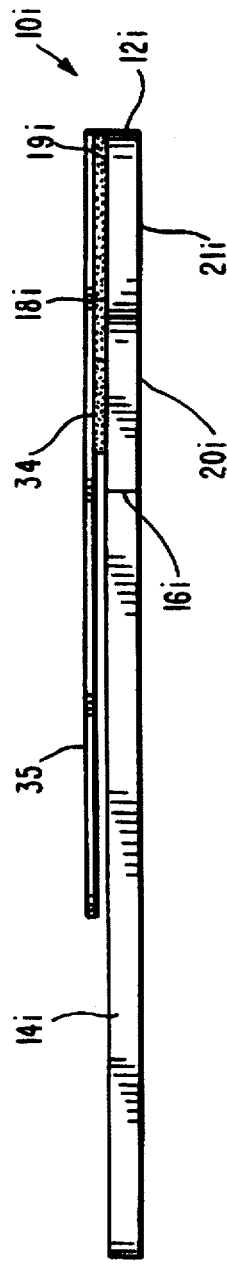
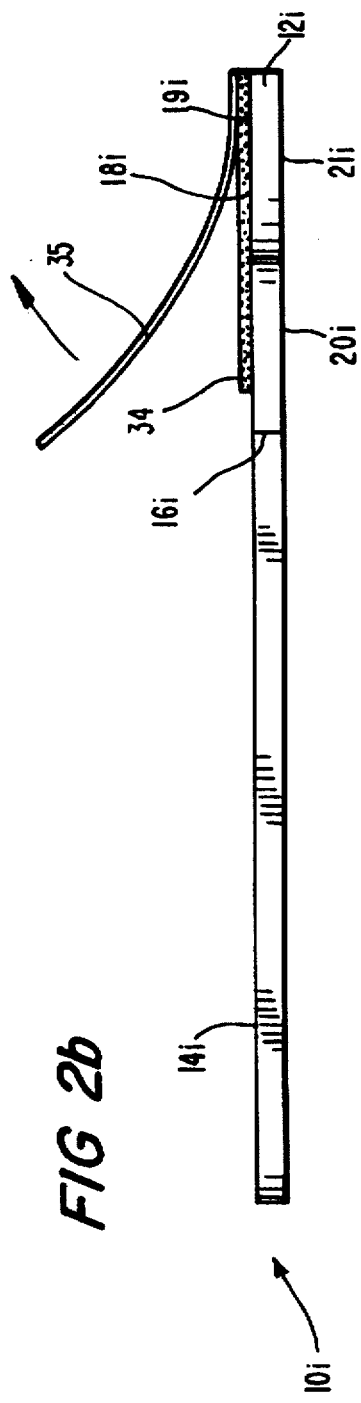

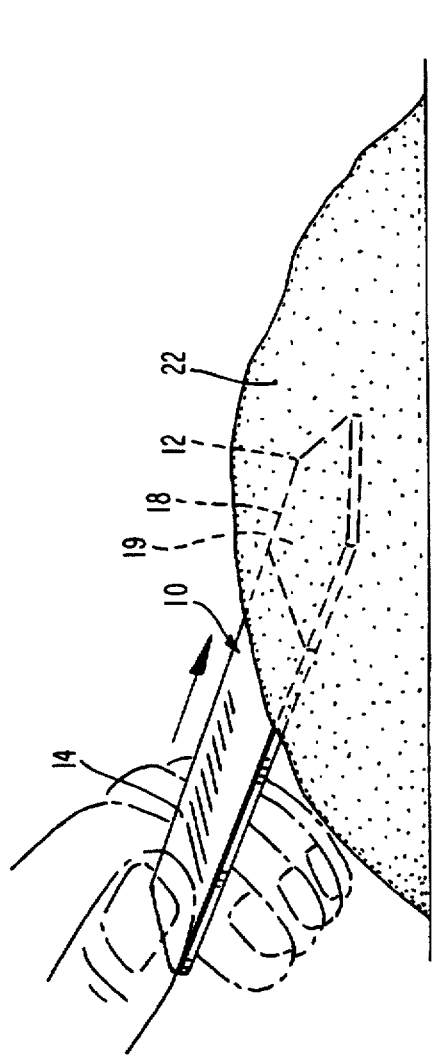
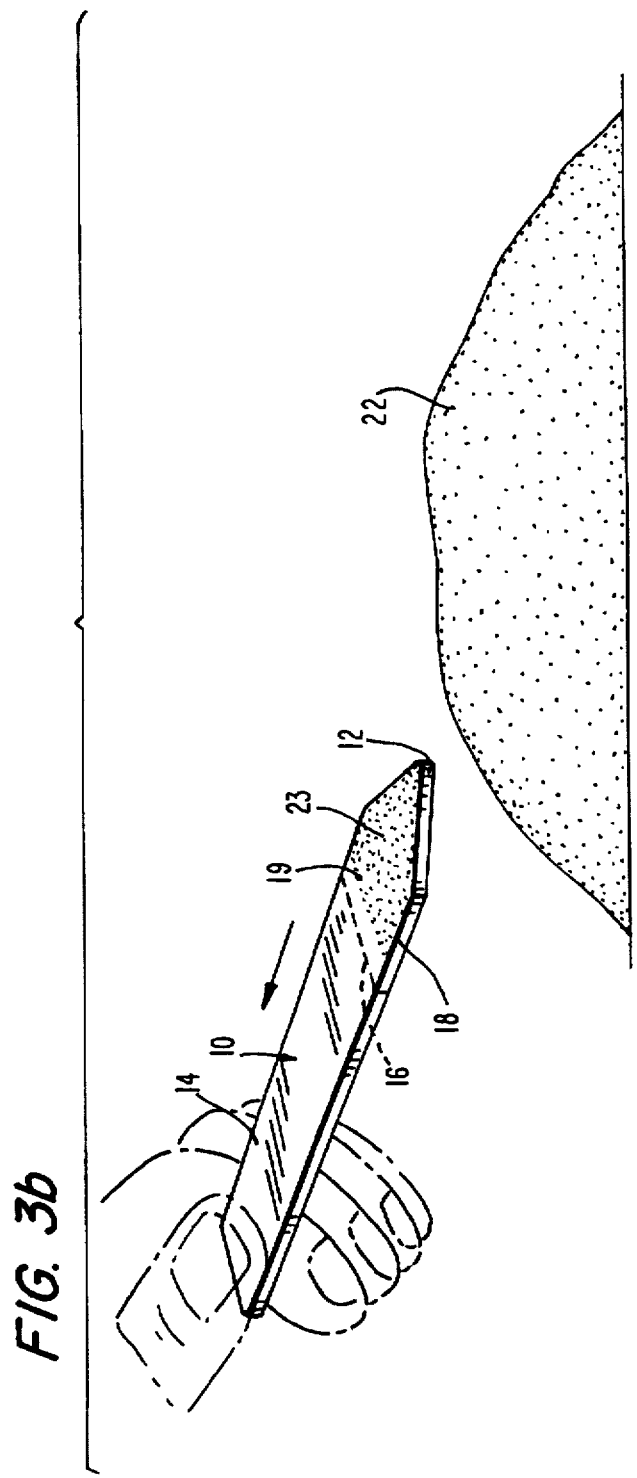
FIG. 3a
FIG. 3b

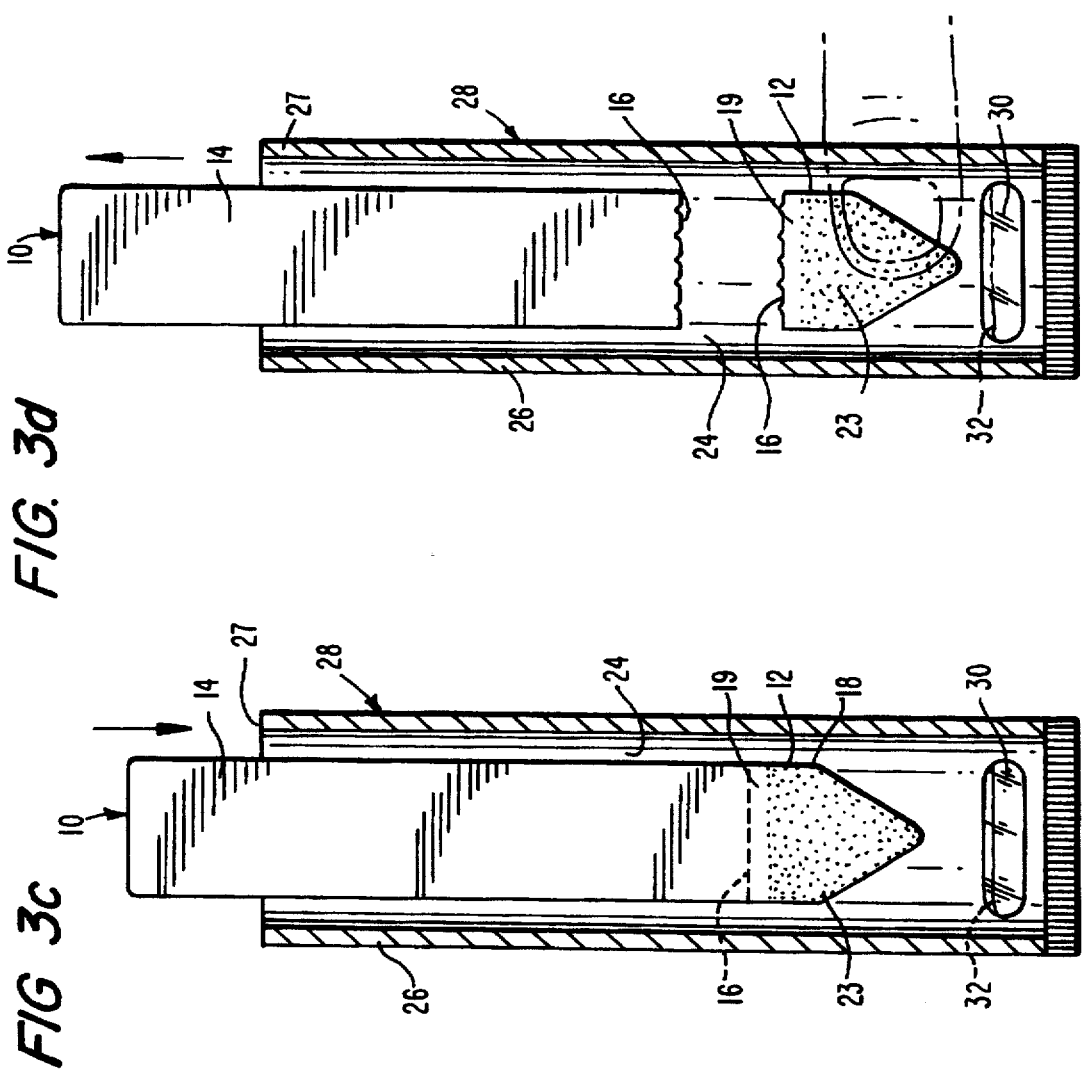

SINGLE USE SAMPLING DEVICE

This is a continuation of application Ser. No. 08/543,638, filed Oct. 16, 1995 now abandoned, which is a Rule 60 Continuation of Ser. No. 08/129,556, filed Sep. 29, 1993 now abandoned, which is an FWC of Ser. No. 07/891,246, filed Jun. 1, 1992 now abandoned.

BACKGROUND OF THE INVENTION

1. Field of Invention

The present invention relates to a sampling device useful for acquiring a sample and introducing it into a test kit. More particularly, this invention relates to a single use sampling device which provides a fresh substantially uncontaminated surface for acquiring a sample and delivering it directly to a test kit without requiring any transfers of the sample.

2. Background of the Invention

In identification testing of unknown materials, particularly in the use by law enforcement personnel who gather specimens which may be used as criminal evidence, acquisition of an accurate sample is of primary importance. Currently, field identification test kits used to screen for the presence of narcotics rely on various reusable sampling devices such as a pen-knife blade, a match stick or a small plastic spoon.

These types of devices which acquire and transfer a sample, rely on the operator to provide a clean uncontaminated surface. In a field environment, there are many opportunities which potentially could lead to cross-contamination and then a false accusation. A need exists to provide a single use sampling device to be used with the available test kits to collect and deliver adequate uncontaminated samples.

There are numerous strip type diagnostic tests available, but in most cases, the strip also contains reagents. Exemplary of these are the following. Wie et al., U.S. Pat. No. 4,900,663, which teaches a test card incorporating a colorimetric indicator test to determine the presence of a minute amount of a specific substance in a liquid medium.

Grage, U.S. Pat. No. 5,082,626, teaches a wedge shape test strip system useful in analyzing test samples such as whole blood. The strip has a differential vertical dimension which permits rapid flow and uniform draw through the device with contact of the relevant portion of the sample to a reagent contained on the strip.

As an example of the narcotics screening kits which are available, one kit makes use of Marquis reagent (Sulfuric Acid/Formaldehyde) packaged in unit dose ampoules contained in a single use resealable flexible transparent plastic pouch. The unknown sample is placed in the pouch, the pouch is sealed and the ampoule containing the reagents is crushed, releasing the reagents and initiating a reaction. Any color change is observed and compared to several standards for the subject compounds, which are opium alkaloids, codeine and amphetamine.

Nowhere in the prior art is there anything suggesting a single use strip with separable parts as a mechanism for providing accurate samples to test kits. This need is addressed by the instantly disclosed invention.

SUMMARY OF THE INVENTION

A single use sampling device for a test kit includes a strip having a first part and a second part. The first part has a first side and a second side, each side having a surface which functions as a spatula for collecting and placing the sample into the test kit container. The second part serves as a handle for manipulating the first part. The first part containing the sample is readily separable from the second part so that it may be left in the test kit container. The device provides a clean substantially uncontaminated surface for collecting and delivering a sample into a test kit container with a minimum of manipulation. The device is useful for both dry particulate samples and materials dissolved in a medium capable of evaporation.

BRIEF DESCRIPTION OF THE DRAWINGS

FIG. 1 is a perspective view of the preferred embodiment of the single use sample device of the present invention.

FIGS. 2a–d illustrates an alternate embodiment of the device of the present invention.

FIGS. 3a–e are a series of illustrations of the function of the device of FIG. 1 with a sample and a test kit.

DETAILED DESCRIPTION

Figure 2C:
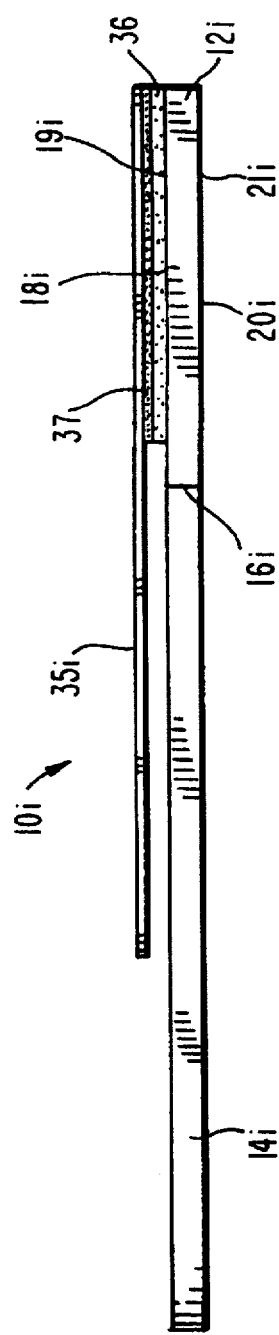

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of this invention will be measured by the appended claims and their equivalents.

FIG. 1 shows a single use test strip 10 having a first part 12 and a second part 14 with a provision 16 for the separation of part 12 from part 14. In the preferred embodiment wherein strip 10 is formed from absorbent chipboard, provision 16 is a perforation. First part 12 has a first side 18 and a second side 20. Side 18 has a surface 19 and side 20 has a surface 21 which serve as a clean spatula for collecting a sample and placing it into a testing container.

FIGS. 2a–b display an alternative embodiment. In this alternative embodiment the structure of the single use sampling device is substantially similar to the sampling device of the embodiment of FIG. 1. Accordingly, substantially similar functions will be numbered identically to those components of the embodiment of FIGS. 1 and 2a–b except a suffix "i" will be used to identify those components in FIGS. 2a–b. In alternative embodiment, sampling device 10i includes second part 14i as a handle for manipulating first part 12i to acquire and transport a sample. First side 18i having surface 19i has a coating of a pressure sensitive adhesive 34 which is protected by a release sheet 35 which is removed prior to use of the device. Adhesive coating 34 ensures rapid effective pick up of an unknown sample, and substantially prevents loss during introduction into the testing tube. The presence of release covering 35 ensures that surface 19i remains substantially uncontaminated.

Figure 2D:
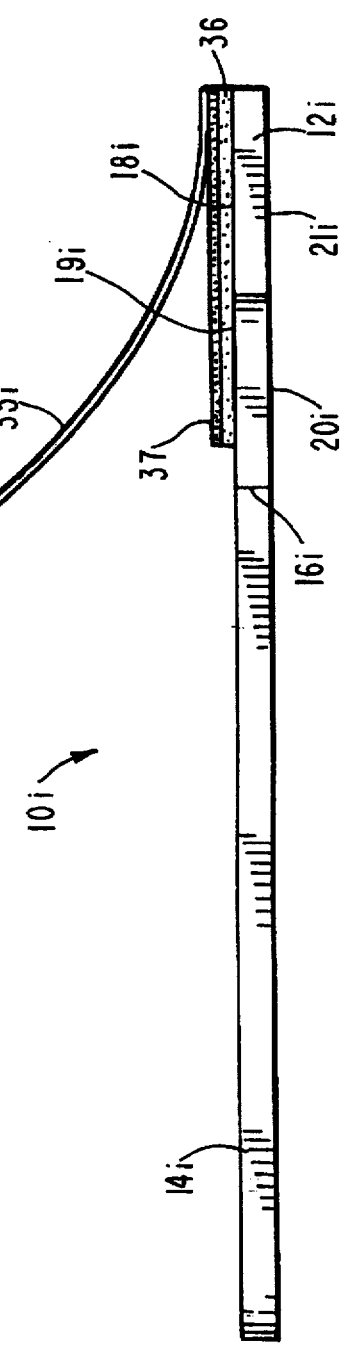

A further refinement of the alternative embodiment of FIGS. 2a–b is shown in FIGS. 2c–d. The same component identification with "i" will be followed as in FIGS. 2a–b. In this embodiment, a layer of foam material 36 is bonded to at least a portion of surface 19i of side 18i of first part 12i. Foam layer 36 preferably has a coating of pressure sensitive adhesive 37 protected by a release covering 35i which substantially ensures that the adhesive coating 37 will be uncontaminated. The presence of the foam layer substantially enhances the sample pick up and retention ability in the case where the sample is an aqueous solution. Adhesive layer 37 substantially ensures good collection and transfer of a dry sample.

FIGS. 3a–e demonstrate the use of sample device 10 in collecting a sample (FIGS. 3a–b) through the various steps (FIGS. 3c–e) of conducting a test. In FIG. 3a, device 10 is placed in unknown substance 22 for the purpose of acquiring a sample 23. In FIG. 3b, sample 23 is seen on surface 19 of first side 18 of part 12 while part 14 is being used as a handle for manipulating the device. In FIG. 3c, device 10 is seen with the collected sample being placed in a test kit 28. This kit includes a flexible tube 26 and an ampoule 30 containing a reagent 32. The part of the device with the sample is introduced into an interior 24 of the tube.

In FIG. 3d, part 12 having sample 23 on surface 19 is separated from part 14 at provision 16 for separation by grasping part 12 through tube 26 of test kit 28 and removing and discarding part 14. FIG. 3e shows a tip 27 of tube 28 being sealed by a clamp 33. Ampoule 30 is crushed, releasing reagent 32, by squeezing tube 28 which initiates a reaction with unknown sample 23.

As was demonstrated by the sequence in FIGS. 3a–e, a clean surface 19 was presented to unknown substance 22 and used to transport sample 23 to contact with reagent 32 without any additional contact.

Single use device 10 can be manufactured from a variety of papers, chipboard, plastic, metal, glass and wood, with the preferred embodiment being an absorbent chipboard to allow use with aqueous samples as well as dry powder samples. In the case of aqueous samples, strip 10 is dipped into the unknown substance and allowed to air dry before placement in the test kit. To remove an unknown substance from a surface, part 12 may be moistened, then rubbed across the surface to acquire the unknown. The strip is then allowed to air dry before placement in the test kit.

It is further preferred that first side 18 of first part 12 be a darker color and second side 20 of first part 12 be a lighter color relative to each other. The purpose of the darker and lighter colors is to allow better visualization of samples for comparison purposes. The provision for separation 16 between part 14 and part 12 can be a perforation, as in the case with the preferred embodiment, an area of reduced thickness or notches at the edges. In the case of other materials, the alternate provisions for separation or a combination thereof may be preferred.

In the alternative embodiment shown in FIGS. 2a–b and the refinement in FIGS. 2c–d, the function of device 10 is identical to that shown in FIGS. 3a–e. One skilled in the art of test kits will recognize that for particular tests and reagent systems, the device material and any adhesive or foam used will need to be selected to as to avoid interference with the particular test being conducted.

Figure 5:
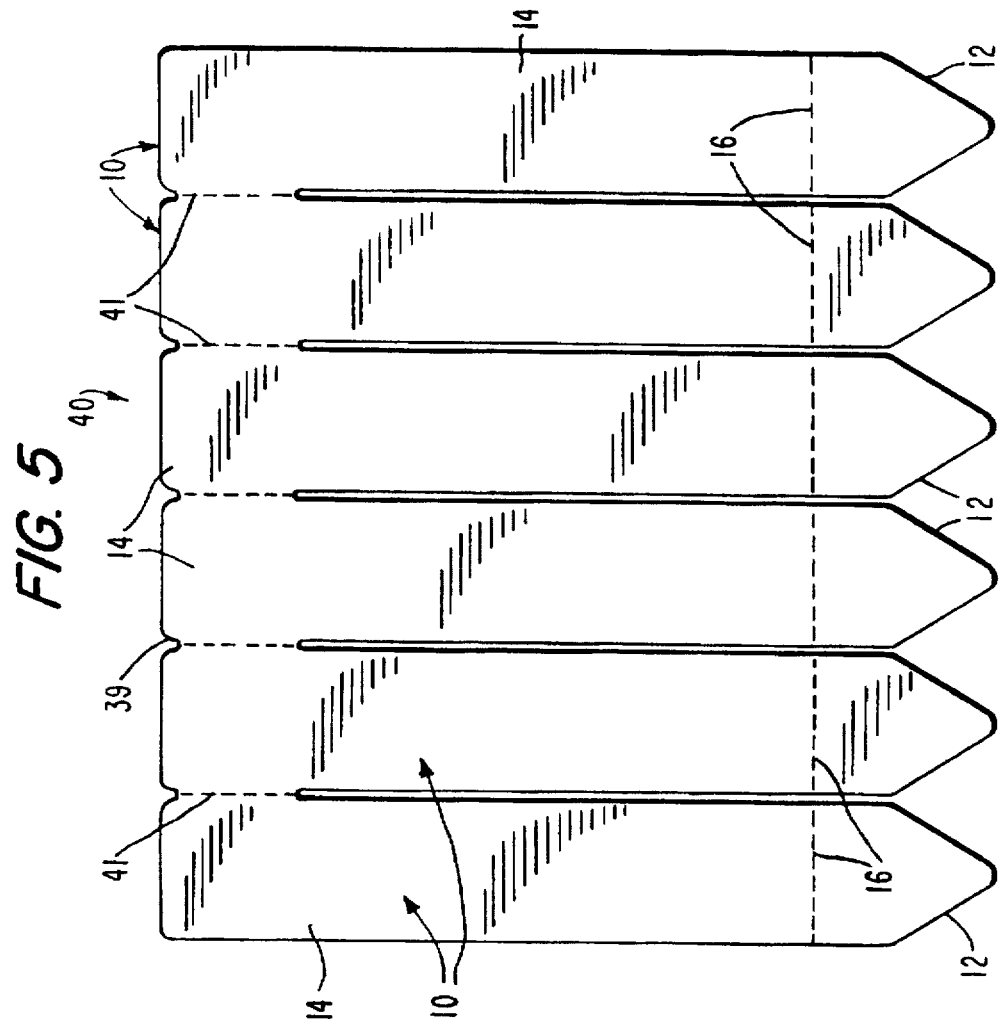
FIG. 5 illustrates a plurality of devices of the present invention joined to form a pack.
Figure 4:
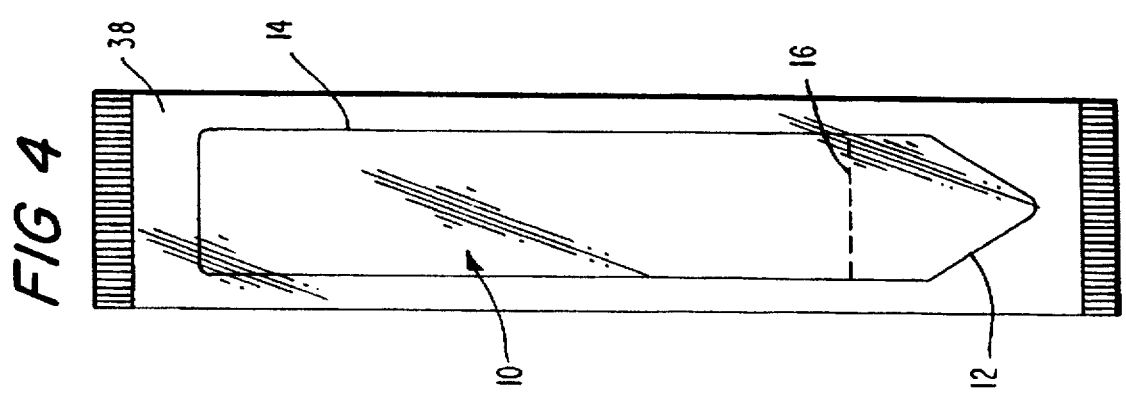
FIG. 4 illustrates an individually packaged device.

Additionally, FIGS. 4 and 5 represent methods of packaging and delivery of single use sampling device 10 applicable to all the embodiments described hereinabove. FIG. 4 shows device 10 individually overpackaged in a package 38. The package may be formed from plastic or cellophane film, paper, metallic foil or the like. FIG. 5 shows a plurality of devices 10 joined at a portion 39 of second part 14 to form a packet 40. Strips 10 are individually detachable by at a provision 41 for detachment which could be perforations, area of reduced thickness or notches at the edge of the strip. In the preferred embodiment where the strip is chipboard, the provision 41 is preferably a perforation, other materials may require the alternates or some combination of them.

A reclosable container could be provided for the strips 10 whether the strips were individual, individually packaged or in a packet containing a plurality of strips. The reclosable overpackage may be formed from plastic, paper, metal or the like.

Thus it can be seen that the present invention provides a simple ready-to-use single use sample collection and transfer device which substantially ensures that an uncontaminated sample is provided to a test kit.

What is claimed is:

1. A single use sampling device for test kit comprising:
   (a) a unitary, one-piece strip divided into interconnected first and second parts, said first and second parts being defined by a line of weakness provided therebetween, said first part having a first side and a second side, each of said sides having a surface to serve as a spatula to collect and deliver a sample into a test kit, said surfaces being formed such that at least a portion of one of said surfaces having a pressure sensitive adhesive applied thereto to facilitate a sample collection phase and a sample delivery phase into the test kit, said second part serving as a handle for manipulating said first part;
   (b) said spatula serving portion and said handle serving portion being separated from each other by grasping and separating along the line of weakness between the two parts after completing the sample collection and delivery phases of the test and prior to a sample assay phase.

2. The device of claim 1 wherein said means includes any one or any combination of perforations, area of reduced thickness and notches.

3. The device of claim 1 wherein said strip is formed from a material selected from the group consisting of paper, chipboard, plastic, metal, glass and wood.

4. The device of claim 1 wherein said first side of said first part has a lighter color and said second side of first part has a darker color relative to each other.

5. A packaged device comprising the device of claim 1 and an overpackage therefor.

6. The device of claim 1 wherein said first part has pressure sensitive adhesive applied to at least a portion of one of said surfaces to aid said sample collection and placement.

7. The device of claim 6 further including a peelable release cover which covers the adhesive on said surface of said strip and protects said adhesive until said cover is removed.

8. The device of claim 1 wherein a plurality of said strips are joined at a portion of said second part to form a packet, further including means for individually detaching said strips from said packet, said means demarcating said strip and weakening the joining of said strips to said packet, thereby facilitating an individual detachment of said strips from said packet.

9. The device of claim 8 wherein said detachment means includes any one or any combination of perforations, area of reduced thickness and notches.

10. A device of claim 1, wherein said first part has a layer of a foamed material bonded on the thereto for collection and placement of an aqueous sample into the test kit.

11. The device of claim 10 wherein said foam has a coating of a pressure sensitive adhesive and a peelable release cover protecting said coating until said cover is removed.

12. A packet of single use sampling devices for test kit comprising:
   a plurality of unitary, one-piece strips divided into interconnected first and second parts, said first and second parts being defined by line of weakness provided therebetween, said first part having a first side and a second side, each of said sides having a surface to serve as a spatula to collect and deliver a sample into a test kit, said surfaces being formed such that at least a portion of one of said surfaces having a pressure-sensitive adhesive applied thereto facilitate a sample collection phase and a sample delivery phase into the test kit, said second part serving as a handle for manipulating said first part;

said spatula serving portion and said handle serving portion being separable from each other by grasping and separating along the line of weakness between the two parts after completion of sample collection and delivery phases of the test prior to a sample assay phase of the test;

said strips being joined at a portion of said second part to form a pack, said strips having a perforation at said juncture for facilitating removal of an individual strip from said pack;

and said strips being formed from an absorbent chipboard having said first side colored a lighter color and said second side colored a darker color relative to each other.

13. A packaged packet comprising the packet of claim 1 and a reclosable overpackage therefor.

* * * * *